United States Patent [19]

Stieber

[11] Patent Number: 4,808,714

[45] Date of Patent: Feb. 28, 1989

[54] SUBSTITUTED DITHIOCARBAMYLUREA ACCELERATORS

[75] Inventor: Joseph F. Stieber, Prospect, Conn.

[73] Assignee: Uniroyal Chemical Company, Inc., Middlebury, Conn.

[21] Appl. No.: 83,912

[22] Filed: Aug. 6, 1987

Related U.S. Application Data

[63] Continuation of Ser. No. 832,278, Feb. 20, 1986, abandoned, which is a continuation-in-part of Ser. No. 585,072, Mar. 1, 1984, Pat. No. 4,631,316.

[51] Int. Cl.$^4$ .................. C07D 279/12; C07D 207/46
[52] U.S. Cl. ................... 544/58.4; 544/160; 548/531; 560/18; 564/40
[58] Field of Search ............ 544/58.4, 158, 159, 544/160; 546/247; 548/531, 567

[56] References Cited

U.S. PATENT DOCUMENTS 3,947,511  3/1976  Raasch .................. 260/545 R

Primary Examiner—Christopher Henderson
Attorney, Agent, or Firm—Raymond D. Thompson

[57] ABSTRACT

Novel substituted dithiocarbamylurea accelerators of the formula $R^1NHC(O)NHSC(S)NR^2R^3$ wherein R is phenyl or substituted phenyl and $R^2$ and $R^3$ are alkyl, aryl or aralkyl or together are alkylene, oxydialkalene or thiodialkylene exhibit unexpectedly improved scorch safety when employed as sulfur cure accelerators. In another aspect, this invention relates to accelerator compositions comprising said accelerators and thiuram or benzothiazole sulfenamide accelerators. In yet another aspect, this invention relates to curable compositions comprising such novel accelerators, sulfur and/or a sulfur donor compound and a sulfur curable rubber.

3 Claims, No Drawings

SUBSTITUTED DITHIOCARBAMYLUREA ACCELERATORS

This is a continuation of application Ser. No. 832,278 filed Feb. 20, 1986 now abandoned which is a continuation-in-part of application Ser. No. 585,072 filed Mar. 1, 1984 now U.S. Pat. No. 4,631,316.

FIELD OF THE INVENTION

This invention is directed to novel dithiocarbamylureas which are useful as sulfur cure accelerator agents. In another aspect, this invention is directed to curable rubber compositions comprising said novel dithiocarbamylureas; sulfur and/or a sulfur donor compound; and a sulfur-curable rubber. In yet another aspect, this invention relates to cure accelerator compositions comprising such novel dithiocarbamylureas and benzothiazole sulfenamides and/or thiurams.

BACKGROUND OF THE INVENTION

The use of sulfur cure accelerators to increase the curing rate of rubber comositions and to thereby improve scorch safety at processing temperatures has long been practiced in the rubber industry.

Thus, for example, U.S. Pat. No. 3,947,511 (Raasch) discloses two classes of compounds useful as sulfur cure accelerators: (1) those of the formula:

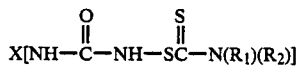

wherein X is alkyl; and (2) those of the formula:

wherein X is alkylene, O- or S-interrupted alkylene, alkenylene, alkylenebis(arylene), arylenebis(alkylene) or arylene.

However, while such prior art sulfur cure accelerators will reduce the cure time and consequently improve scorch safety, it would nonetheless be desirable to possess novel cure accelerators which would further improve scorch safety. It would also be desirable to possess sulfur cure accelerators that would produce cured rubber compositions having enhanced physical properties relative to rubbers cured employing such prior art sulfur cure accelerators.

Coran (U.S. Pat. No. 3,546,185) shows the use of specified sulfenamides which function as inhibitors of premature vulcanization. As is stressed in Coran (see, e.g. column 2, lines 43-45) such inhibitors are employed in combination with an accelerator to increase scorch safety by retarding cure.

Matoba (U.S. Pat. No. 4,268,640) discloses a curable composition comprising a halogen-containing polymer and a substituted mono- or di-thiobiurea which functions as a cross-linking agent.

It is an object of this invention to provide novel cure accelerators which would provide increased scorch safety in the production of cured rubber compounds.

It is a further object of this invention to provide a curable rubber composition which incoporates such improved sulfur cure accelerators.

It is another object of this invention to provide a sulfur cure accelerator which, when employed in rubber, will produce rubber compositions having desirable elastomeric properties.

The foregoing objects and additional objects will become more fully apparent from the following description and accompanying Examples.

DESCRIPTION OF THE INVENTION

In one aspect, this invention relates to novel compounds useful as sulfur-cure accelerators, which compounds are of formula I below:

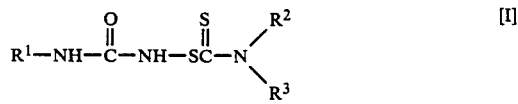

wherein $R^1$ is phenyl or phenyl substituted with one or more members selected from the group consisting of:
halogen,
$C_1$-$C_{12}$ alkyl,
$C_1$-$C_8$ alkoxy,
$C_1$-$C_8$ alkylthio,
isocyanato,
methylenedioxy,
$NR^4R^5$, wherein $R^4$ and $R^5$ are each independently hydrogen or $C_1$-$C_6$ alkyl,
$COOR^6$, wherein $R^6$ is $C_1$-$C_{12}$ alkyl, and
$NHCOOR^7$, wherein $R^7$ is $C_1$-$C_8$ alkyl; and
$R^2$ and $R^3$ are each independently $C_1$-$C_{18}$ alkyl, $C_5$-$C_6$ cycloalkyl, phenyl or $C_7$-$C_9$ aralkyl; or
$R^2$ and $R^3$ taken together are $C_4$-$C_6$ alkylene, $C_3$-$C_4$ oxydialkylene or $C_3$-$C_4$ thiodialkylene.

In another aspect, this invention is directed to a curable rubber composition comprising:

(A) an accelerator compound having the formula:

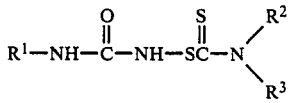

wherein $R^1$ is phenyl or
phenyl substituted with one or more members selected from the group consisting of:
halogen,
$C_1$-$C_{12}$ alkyl,
$C_1$-$C_8$ alkoxy,
$C_1$-$C_8$ alkylthio,
isocyanato,
methylenedioxy,
$NR^4R^5$, wherein $R^4$ and $R^5$ are each independently hydrogen or $C_1$-$C_6$ alkyl,
$COOR^6$, wherein $R^6$ is $C_1$-$C_{12}$ alkyl, and
$NHCOOR^7$, wherein $R^7$ is $C_1$-$C_8$ alkyl; and
$R^2$ and $R^3$ are each independently $C_1$-$C_{18}$ alkyl, $C_5$-$C_6$ cycloalkyl, phenyl or $C_7$-$C_9$ aralkyl or
$R^2$ and $R^3$ taken together are $C_4$-$C_6$ alkylene, $C_3$-$C_4$ oxydialkylene or $C_3$-$C_4$ thiodialkylene;
with the proviso that when $R^2$ and $R^3$ are methyl, $R^1$ is not phenyl;

(B) at least one member selected from the group consisting of sulfur and sulfur donor compounds; and (C) at least one sulfur-curable rubber.

In yet another aspect, this invention is directed to a cure accelerator composition comprising:

(A) a compound having the formula:

$$R^1-NH-\overset{\overset{O}{\|}}{C}-NH-\overset{\overset{S}{\|}}{SC}-N\overset{R^2}{\underset{R^3}{\diagdown}}$$

wherein $R^1$ is phenyl or phenyl substituted with one or more members selected from the group consisting of:
  halogen,
  $C_1$-$C_{12}$ alkyl,
  $C_1$-$C_8$ alkoxy,
  $C_1$-$C_8$ alkylthio,
  isocyanato,
  methylenedioxy,
  $NR^4R^5$, wherein $R^4$ and $R^5$ are each independently hydrogen or $C_1$-$C_6$ alkyl,
  $COOR^6$, wherein $R^6$ is $C_1$-$C_{12}$ alkyl, and
  $NHCOOR^7$, wherein $R^7$ is $C_1$-$C_8$ alkyl; and $R^2$ and $R^3$ are each independently $C_1$-$C_{18}$ alkyl, $C_5$-$C_6$ cycloalkyl, phenyl or $C_7$-$C_9$ aralkyl or $R^2$ and $R^3$ taken together are $C_4$-$C_6$ alkylene, $C_3$-$C_4$ oxydialkylene or $C_3$-$C_4$ thiodialkylene; and (B) at least one compound selected from the group consisting of benzothiazole sulfenamides and thiurams.

The sulfur-cure accelerator compounds of this invention are of the formula:

$$R^1-NH-\overset{\overset{O}{\|}}{C}-NH-\overset{\overset{S}{\|}}{SC}-N\overset{R^2}{\underset{R^3}{\diagdown}}$$

wherein $R^1$, $R^2$ are $R^3$ are as defined above in formula I.

Preferably, such compounds are of the above-described formula wherein:

$R^1$ is phenyl or phenyl substituted with one or more members of the group consisting of:
  fluorine,
  chlorine,
  bromine,
  isocyanato,
  $C_1$-$C_2$ alkyl,
  $C_1$-$C_2$ alkoxy,
  $C_1$-$C_2$ alkylthio,
  $NR^4R^5$ wherein $R^4$ and $R^5$ are methyl,
  $COOR^6$ wherein $R^6$ is $C_1$-$C_2$ alkyl, and
  $NHCOOR^7$ wherein $R^7$ is $C_1$-$C_2$ alkyl; and $R^2$ and $R^3$ are each independently $C_1$-$C_{12}$ alkyl, $C_5$-$C_6$ cycloalkyl or benzyl; or $R^2$ and $R^3$ taken together are tetramethylene, pentamethylene, oxydiethylene or thiodiethylene.

Most preferably:

$R^1$ is phenyl or phenyl substituted with one or more members selected from the group consisting of:
  chlorine,
  methyl,
  methoxy,
  methylthio,
  dimethylamino,
  isocyanato,
  methoxycarbonyl,
  methoxycarbonylamino; and $R^2$ and $R^3$ are the same and are $C_1$-$C_4$ alkyl, cyclohexyl or benzyl; or $R^2$ and $R^3$ taken together are oxydiethylene.

The compounds of this invention may be produced by reacting a sulfenamide having the formula:

$$H_2N\overset{\overset{S}{\|}}{SC}-N\overset{R^2}{\underset{R^3}{\diagdown}}$$

wherein $R^2$ and $R^3$ are as defined above, and an aryl isocyanate of the formula:

$$R^1(NCO)_n$$

wherein $R^1$ is as defined above and n is 1 or 2.

The reactants are typically mixed together in molar equivalents in the presence of a suitable inert solvent. Suitable solvents which may be employed include aliphatic and aromatic hydrocarbons such as hexane, isooctane, benzene, toluene and xylene, and their halogenated derivatives such as chloroform, carbon tetrachloride, 1,1,1-trichloroethane, trichlorotrifluoroethane, and chlorobenzene or ethers. The reactants can also be contacted in melt form if desired. In large-scale preparations, however, the use of an inert solvent is advantageous to aid in control of the reaction.

The reaction is conveniently carried out at temperatures of between about 10° C. and about 130° C., preferably of between about 25° C. and about 110° C., most preferably of between about 70° C. and about 90° C. Reaction pressure is not critical, with ambient pressure typically being employed.

The reaction proceeds in the presence or absence of catalysts. Catalysts are advantageous in enabling the use of lower temperatures and/or shorter reaction times. Suitable catalysts which may be employed include alkyltin dialkanoates, such as dibutyltin dilaurate; as well as tertiary amines such as trimethylamine, triethylamine, tripropylamine, tetramethylethylene-diamine, 1,4-diazabicyclo[2,2,2]octane, and pyridine.

The products may recovered from the reaction mass employing conventional methods, such as filtration and evaporation. If desired, the products may be purified by recrystallization from known organic solvents.

The curable rubber compositions of this invention are comprised of (A) an effective amount of the sulfur cure accelerator of this invention; (B) at least one member selected from the group consisting of sulfur and sulfur donor compounds; and (C) at least one sulfur-curable rubber.

The sulfur donor compounds which may be employed (as an alternative or in addition to sulfur) as component (B) of the curable rubber compositions of this invention are well known to those skilled in the art of rubber compounding. Illustrative of such sulfur donor compounds are 2-(4-morpholinyldithio)benzothiazole, dipentamethylene thiuram hexasulfide, N,N'-caprolactam disulfide and the like.

The curable-rubber component of the composition may be comprised of any sulfur-curable rubber. Illustrative of the rubbers which may be employed are uncured natural rubber, cis-polyisoprene, trans-polyisoprene, polybutadiene, styrene-butadiene copolymer, acrylonitrile-butadiene copolymer, neoprene, ethylene-propylene-nonconjugated diene terpolymer, and mixtures thereof.

These curable rubber compositions are produced by blending the appropriate amounts of curative, accelerator and rubber by means conventional in the art of rubber compounding, such as Banbury ™ mixers and the like.

The novel sulfur cure accelerators of this invention are present in amounts effective to accelerate the cure of the rubber to the desired extent. Typically, such accelerators are present in amounts of between about 0.05 and about 10 parts by weight per 100 parts by weight of rubber (phr), component (C). Preferably, such accelerators are present in amounts of between about 0.3 and about 3 phr, most preferably of between about 0.3 and about 2 phr.

The amount of sulfur and/or sulfur donor curative which may be added will depend on a number of factors including the particular curative employed, the particular rubber to be cured, the extent of cure desired, and the like. However, the preferred amount of curative for any given application may be readily determined by one skilled in the art by routine experimentation.

In addition to the sulfur cure accelerator, sulfur and/or sulfur donor and sulfur-curable rubber, the compositions of this invention may further comprise reinforcing agents, fillers, processing aids, extender oils, plasticizers, antioxidants, ultraviolet stabilizers, and the like, all of which additional components (e.g. zinc oxide, stearic acid, etc.) are well known to those skilled in the rubber art.

Moreover, it has been found that the novel substituted dithiocarbamylurea accelerators of this invention exhibit unexpectedly improved results when employed in conjunction with benzothiazole sulfenamides or thiruams. Specifically, unexpectedly enhanced scorch safety is achieved when the accelerators of this invention are employed in conjunction with benzothiazole sulfenamides whereas unexpectedly enhanced deformation resistance is exhibited when such accelerators are employed in conjunction with a thiuram.

Suitable benzothiazole sulfenamides which may be employed in conjunction with the novel accelerators of this invention include N,N-diethyl-2-benzothiazole sulfenamide, N,N-dicyclohexyl-2-benzothiazole sulfenamide, N-oxydiethylene-2-benzothiazole sulfenamide, N-tert-butyl-2-benzothiazole sulfenamide, N-cyclohexyl-2-benzothiazole sulfenamide, 2-(4-morpholino)dithiobenzothiazole sulfenamide and the like.

Thiurams which may be used with the compounds of this invention include tetramethylthiuram monosulfide, tetramethylthiuram disulfide, dipentamethylenethiuram disulfide, dipentamethylenethiuram tetrasulfide, dipentamethylenethiuram monosulfide, tetrabutylthiuram disulfide, tetrabutylthiuram monosulfide, tetraethylthiuram monosulfide, tetraethylthiuram disulfide, and the like.

The ratios of novel dithiocarbamylurea accelerator to benzothiazole sulfenamide or thiuram which may be employed will vary in accordance with a number of factors (e.g. the specific accelerators employed, the curative employed, the rubber to be cured, etc.), such ratios being readily determined by routine experimentation. However, typically, the molar ratio of novel cure accelerator to benzothiazole sulfenamide or thiuram in the curing accelerator compositions of this invention will range between about 100:1 and about 1:10, preferably between about 10:1 and about 1:5, and most preferably between about 5:1 and about 1:1.

The novel cure accelerators of this invention, particularly when employed in the cure accelerator compositions of this invention, will provide desirable scorch safety coupled with desirable elastomeric properties in the cured rubber.

EXAMPLES

The following Examples are intended to further illustrate the invention and are not intended to limit the scope of the invention in any manner.

Example 1

Preparation of N,N-dimethylthiocarbamylthio-N'-phenylurea (Compound No. 1)

A quantity of S-dimethylthiocarbamyl sulfenamide was prepared according to the method of G. Smith et al, J. Org. Chem., 14, 935–45 (1949)—i.e. by the oxidation of sodium dimethylthiocarbamate in concentrated ammonia solution using aqueous sodium hypochlorite. Phenyl isocyanate (23.8 grams, 0.20 mole) and dibutyltin di-2-ethylhexanoate (0.40 grams) were added to a solution of S-dimethylthiocarbamate sulfenamide in toluene (400 ml). The mixture was stirred and heated on a steam bath at 85°–95° C. for 2.5 hours. The slurry so formed was filtered and the white solid product was washed with hot tetrahydrofuran and dried in a 60° C. oven. Yield: 42.8 grams, melting point 193°–194° C.

Example 2

N-dimethylthiocarbamylthio-N'-(3-methoxycarbonylamino-4-methylphenyl)urea (Compound No. 7)

Toluene-2,4-diisocyanate (17.9 grams, 0.10 mole) and dibutyltin di-2-ethylhexanoate (0.20 grams) were dissolved in toluene (100 ml). The solution was heated to 75° C., and a solution of S-(dimethylthiocarbamyl)sulfenamide (13.6 grams, 0.10 mole) in toluene (200 ml) was slowly added, with constant stirring, over a period of 45 minutes. When the addition was complete, the mixture was maintained at 70° C.–80° C. and stirred for an additional hour. Then anhydrous methanol (15 ml) was added. The slurry was cooled to room temperature and filtered. The white powdery product was dried at 60° C. Yield 30.5 grams, melting point 180°–185° C. IR and NMR spectra were consistent with the assigned structure.

Employing a process essentially identical to those employed in Examples 1 and 2 additional compounds within the scope of this invention (Compounds 2–6 and 8–10) were produced. These formulae and melting points of the compounds are listed in Table I.

TABLE I

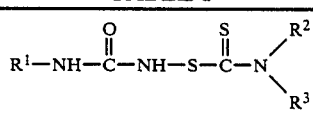

| Cpd. No. | R¹ | R² | R³ | m.p. °C. |
|---|---|---|---|---|
| 1 | C₆H₅ | CH₃ | CH₃ | 193–194 |
| 2 | C₆H₅ | C₄H₉ | C₄H₉ | 120–122.5 |

TABLE I-continued

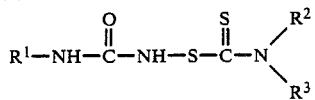

| Cpd. No. | R¹ | R² | R³ | m.p. °C. |
|---|---|---|---|---|
| 3 | $C_6H_5$ | $c\text{-}C_6H_{11}$ | $c\text{-}C_6H_{11}$ | 173–176 |
| 4 | $C_6H_5$ | —$CH_2CH_2$—O—$CH_2$—$CH_2$— | | 165 |
| 5 | $C_6H_5$ | $CH_2C_6H_5$ | $CH_2C_6H_5$ | 202–203 |
| 6 | $4\text{-}ClC_6H_4$ | $CH_3$ | $CH_3$ | 177–180 |
| 7 | $3\text{-}NHCOOCH_3\text{-}4\text{-}CH_3C_6H_3$ | $CH_3$ | $CH_3$ | 180–185 |
| 8 | $4\text{-}CH_3C_6H_4$ | $CH_3$ | $CH_3$ | 188–190 |
| 9 | $3,4\text{-}Cl_2C_6H_3$ | $CH_3$ | $CH_3$ | 185–186 |
| 10 | $3\text{-}Cl, 4\text{-}CH_3C_6H_3$ | $CH_3$ | $CH_3$ | 176–179 |

Employing a process essentially identical to that described in Examples 1 and 2, the following compounds listed in Table II are prepared.

TABLE II

| Compound No. | R¹ | R² | R³ |
|---|---|---|---|
| 11 | $2\text{-}BrC_6H_4$ | —$(CH_2)_4$— | |
| 12 | $4\text{-}C_{12}H_{25}C_6H_4$ | —$CH_2CH_2$—S—$CH_2$— | |
| 13 | $3\text{-}[N(C_6H_{13})_2]C_6H_4$ | $CH_3$ | $C_{18}C_{37}$ |
| 14 | $3\text{-}[N(CH_3)_2]C_6H_4$ | —$CH_2CH_2$—S—$CH_2CH_2$— | |
| 15 | $3\text{-}(NHCOOC_8H_{17})C_6H_4$ | $CH_3$ | $CH_3$ |
| 16 | $4\text{-}COOCH_3\text{-}C_6H_4$ | $n\text{-}C_4H_9$ | $n\text{-}C_4H_9$ |
| 17 | $3,4\text{-}(CH_3O)_2C_6H_3$ | $C_{12}H_{25}$ | $CH_3$ |

In the following Examples several compounds of this invention were evaluated as curing agents. In such Examples the following abbreviations are employed:

| | |
|---|---|
| SBR | oil extended (37.5 pph) styrene (23.5%)-butadiene (76.5%) copolymer, ML-4 ca. 55 at 100° C. |
| Cis-BR: | cis-polybutadiene |
| Sundex [trademark] Sun Oil Company 790 oil: | aromatic oil |
| Circosol [trademark] Sun Oil Company 4240 oil: | aromatic oil |
| Antiozonant: | N—phenyl-N'—1,3-dimethylbutyl-p-phenylenediamine, Flexzone [trademark] 7F Uniroyal Chemical Company, Inc., antiozonant. |
| Scorch Time: | Mooney Scorch Time measured in minutes at temperature indicated; ASTM D1646. |
| Cure Time: | Time (in minutes) to obtain 90% of cure at temperature indicated; ASTM D2084. |
| Wax: | Sunproof [trademark] improved wax, Uniroyal Chemical Company, Inc. microcrystalline wax. |

Examples 3–6

A masterbatch having the below-listed composition (all in parts by weight) was prepared on a two-roll mill:

| | |
|---|---|
| SBR | 89.4 |
| Cis-BR | 35.0 |
| Zinc Oxide | 3.0 |
| Stearic acid | 1.5 |
| N339 Carbon black | 75.0 |
| Sundex 790 oil | 20.0 |
| Antiozonant | 3.0 |
| Sulfur | 1.9 |
| Total | 228.8 |

This masterbatch was compounded into the curable rubber composition of this invention by the addition of an accelerator compound as indicated in Table III. The composition so formed was tested for its Mooney scorch at 135° C. and, after curing for 10 minutes at 177° C., for its physical properties.

The results are summarized in Table III.

TABLE III

| Example | 3 | 4 | 5 | 6 |
|---|---|---|---|---|
| Masterbatch | 228.8 | 228.8 | 228.8 | 228.8 |
| Cpd. No. | | | | |
| 1 | 1.25 | — | — | — |
| 2 | — | 1.25 | — | — |
| 3 | — | — | 1.25 | — |
| 5 | — | — | — | 1.25 |
| Mooney Scorch, 135° C., min | 35.3 | 26.3 | 26.5 | 38.0 |
| Cure Time* 177° C., min | 6.0 | 8.5 | 9.8 | 9.5 |
| 300% Modulus, mPa | 7.03 | 5.31 | 4.07 | 5.55 |
| Tensile strength, mPa | 18.41 | 17.48 | 14.07 | 17.44 |
| Elongation, % | 630 | 735 | 720 | 705 |

*Time until 90 percent cure obtained.

The above data indicate that the compounds of this invention provide safe, extended scorch times while providing excellent physical properties at a practical cure rate.

Examples 7–9

A masterbatch having the below-listed composition (all in parts by weight) was prepared on a two-roll mill:

| | |
|---|---|
| SBR | 89.4 |
| Cis-BR | 35.0 |
| N339 Carbon Black | 65.0 |
| Zinc Oxide | 3.0 |
| Antiozonant | 3.0 |
| Stearic Acid | 1.5 |
| Wax | 1.5 |
| TOTAL | 198.4 |

This masterbatch was compounded into the curable rubber composition of this invention by the addition of an accelerator compound and sulfur as indicated in Table IV. The composition so formed was tested for its Mooney scorch at 135° C. and, after curing for 10 minutes at 177° C., for its physical properties.

The results are summarized in Table IV.

TABLE IV

| Example | 7 | 8 | 9 |
|---|---|---|---|
| Masterbatch | 198.4 | 198.4 | 198.4 |
| Compound No. | | | |
| 8 | 1.0 | — | — |
| 9 | — | 1.0 | — |
| 10 | — | — | 1.0 |
| Sulfur | 1.9 | 1.9 | 1.9 |
| Mooney Scorch, 135° C., min | 28.3 | 22.8 | 24.0 |
| Cure Time*, 177° C., min | 4.4 | 4.9 | 4.4 |
| 300% Modulus**, psi | 1600 | 1270 | 1500 |
| Tensile**, psi | 3030 | 3090 | 3030 |
| Elongation %** | 550 | 600 | 550 |

*Time until 90 percent cure obtained.
**After 15 minutes at 177° C.

Example 10 and Comparative Experiment A

A masterbatch comprising the following ingredients was compounded on a two-roll mill.

| | |
|---|---|
| SBR | 89.4 |
| Cis-BR | 35.0 |
| N339 Carbon Black | 65.0 |
| Zinc Oxide | 3.0 |
| Antiozonant | 3.0 |
| Stearic Acid | 1.5 |
| Wax | 1.5 |
| TOTAL | 198.4 |

To a 198.4 parts of the above Masterbatch were added 1.9 parts of sulfur and 1.0 part of either Compound 1 (Example 10, within the scope of this invention) or of Compound A (Comparative Experiment A), within the scope of U.S. Pat. No. 3,947,511 to Raasch. The compositions so produced were tested for their Mooney scorch time, cure time and cured properties. The results of such testing are summarized in Table V. Compound 1 and Compound A possess the following structures:

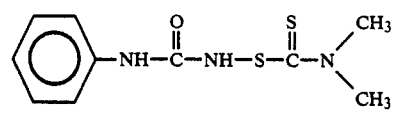

Compound 1:

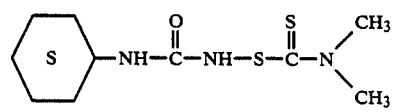

Compound A:

TABLE V

| Example or Comparative Experiment | 10 | A |
|---|---|---|
| Accelerator | Compound No. 1 | Compound A |
| Mooney Scorch Time (124° C.) (Min.) | 29.3 | 23.3 |
| Cure Time* (177° C.) (Min.) | 4.6 | 5.1 |
| 300% Modulus (psi)** | 1790 | 1700 |
| Tensile Strength (psi)** | 3070 | 1990 |
| Elongation %** | 500 | 380 |

*Time until 90% cure achieved.
**Cured properties after 15 minutes at 177° C.

The above data illustrate the improved scorch safety afforded by the compounds of this invention. Such data also indicate the unexpectedly improved physical properties of styrene-butadiene rubber cured with the accelerator of this invention relative to composition cured with prior art accelerators having similar structure.

Example 11 and Comparative Experiment B

A masterbatch having the below-listed composition (in parts by weight) was prepared on a two-roll mill.

| | |
|---|---|
| Natural rubber | 100.0 |
| N234 Carbon Black | 50.0 |
| Circosol 4240 oil | 5.0 |
| Antiozonant | 3.0 |
| Wax | 1.5 |
| Zinc oxide | 3.0 |
| Stearic acid | 2.5 |
| Sulfur | 2.5 |
| Total | 167.5 |

To 167.5 parts of the above masterbatch were added 0.6 part of compound 7 (Example 11—within the scope of this invention) as of Compound B (Comparative Experiment B—within the scope of U.S Pat. No. 3,947,511). The compounds were tested as in Example 10, and the results are summarized in Table VI below.

Compounds 7 and B possess the following structures:

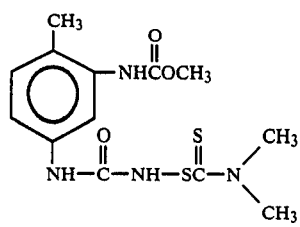

Compound 7:

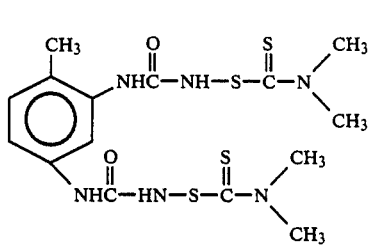

Compound B:

TABLE VI

| Example or Comparative Experiment | 11 | B |
|---|---|---|
| Accelerator | Compound No. 7 | Compound B |
| Mooney Scorch Time* (124° C.) (Min) | 30.0 | 46.3 |
| Cure Time (177° C.) (Min) | 3.0 | 6.6 |
| 300% Modulus, mPa** | 9.7 | 8.4 |
| Tensile Strength, mPa** | 19.2 | 15.4 |
| Elongation, %** | 510 | 500 |

*Time until 90% cure achieved.
**Properties after 15 minutes at 177° C.

The above comparative data clearly demonstrate the improved cure time and enhanced properties afforded by the novel cure accelerators of this invention.

Example 12 and Comparative Experiment C

A comparison study was undertaken between Compound No. 1 of this invention (Example 12) and a well known accelerator, N,N-oxydiethylenebenzothiazole sulfenamide (OBTS) (Comparative Experiment C) employing the following masterbatch:

| | |
|---|---|
| SBR | 84.4 |
| Cis-BR | 35.0 |
| Zinc Oxide | 3.0 |
| Stearic acid | 1.5 |
| N339 Carbon black | 75.0 |
| Sundex 790 oil | 20.0 |
| Antiozonant | 3.0 |
| Wax | 1.5 |
| Sulfur | 1.9 |

The compounded stock was cured for 10 minutes at 177° C. before measuring physical properties.

TABLE VII

| Example or Comparative Experiment | 12 | C |
|---|---|---|
| Masterbatch | 228.4 | 228.4 |
| Cpd. No. 1 | 1.2 | — |
| OBTS | — | 1.2 |
| Mooney Scorch, (135° C.),(min) | 36.0 | 27.8 |
| Cure Time* 177° C., min | 4.3 | 5.8 |
| 300% Modulus,** mPa | 7.9 | 7.6 |
| Tensile strength,** mPa | 18.1 | 18.1 |
| Elongation,** % | 615 | 625 |

*Time at 177° C. until 90% cure obtained.
**Properties measured after 10 minutes at 177° C.

The above data indicate that the composition of this invention exhibits superior scorch time and reduced cure time relative to the commonly employed accelerator OBTS while achieving essentially the same physical properties.

Examples 13-15 and Comparative Experiments D, and E

In order to show the unexpectedly improved activity realized by the use of the accelerators of this invention when used in combination with benzothiazole sulfenamide accelerators, a masterbatch having the following composition was compounded:

| | |
|---|---|
| SBR | 89.4 |
| Cis-BR | 35.0 |
| Stearic acid | 1.5 |
| N339 Carbon black | 65.0 |
| Zinc Oxide | 3.00 |
| Antiozonant | 3.00 |
| Sunproof Improved Wax | 1.50 |
| Total | 198.40 |

This masterbatch was compounded with various amounts of accelerators and sulfur as indicated in Table VIII below. The time until a 90% cure was determined for each composition and the results tabulated in Table VIII below.

TABLE VIII

| Example or Comparative Experiment | 13 | D | 14 | E | 15 |
|---|---|---|---|---|---|
| Masterbatch | 198.4 | 198.4 | 198.4 | 198.4 | 198.4 |
| Compound 1 | 1.02 | — | .51 | — | .51 |
| OBTS* | — | 1.01 | .50 | — | — |
| CBS** | — | — | — | 1.06 | .53 |
| Sulfur | 1.92 | 1.92 | 1.92 | 1.92 | 1.92 |
| Total | 201.34 | 201.33 | 201.33 | 201.38 | 201.36 |
| Cure Time 160° C. | 13.8 | 12.8 | 11.3 | 11.4 | 10.5 |

*N,N—oxydiethylenebenzothiazole sulfenamide
**N—cyclohexyl-2-benzothiozole sulfenamide The above data indicate the unexpected synergistically reduced cure time required when the accelerators of this invention are employed in combination with benzothiazole sulfenamide accelerators.

Examples 16 and 17 and Comparative Experiment F

In order to show the unexpectedly improved deformation resistance realized when the novel accelerators of this invention are used in combination with a thiuram accelerator a masterbatch having the following composition was compounded:

| | |
|---|---|
| SBR 1712 | 89.40 |
| Cis-BR | 35.00 |
| N339 Carbon black | 65.0 |
| Zinc Oxide | 3.00 |
| Antiozonant | 3.00 |
| Stearic Acid | 1.50 |
| Sunproof Improved Wax | 1.50 |
| Total | 198.40 |

This masterbatch was compounded with various amounts of accelerators and sulfur as indicated in Table IX below. The deformation resistance (i.e., 300% modulus) of each composition was determined and the results tabulated in Table IX below.

TABLE IX

| Example or Comparative Experiment | 16 | F | 17 |
|---|---|---|---|
| Masterbatch | 198.40 | 198.40 | 198.40 |
| Sulfur | 1.92 | 1.92 | 1.92 |
| Compound 1 | 1.02 | — | .54 |
| TMTM* | — | .83 | .42 |
| Total | 201.34 | 201.15 | 201.28 |
| 300% Modulus (psi) (after 10 min. @ 177° C.) | 1310 | 1560 | 1800 |

*TMTM = tetramethylthiuram monosulfide

The above data indicate the unexpectedly improved deformation resistance obtained when the compounds of this invention are employed in conjunction with thiurams.

What is claimed is:

1. A compound of the formula:

$$R^1-NH-\overset{\overset{O}{\|}}{C}-NH-\overset{\overset{S}{\|}}{SC}-N\diagdown^{R^2}_{R^3}$$

wherein
R$^1$ is phenyl, or phenyl substituted with one or more members of the group consisting of:
fluorine,
chlorine,
bromine,
isocyanato,
$C_1$-$C_2$ alkyl,
$C_1$-$C_2$ alkoxy,
$C_1$-$C_2$ alkylthio, $NR^4R^5$ wherein $R^4$ and $R^5$ are methyl,
$COOR^6$ wherein $R^6$ is $C_1$–$C_2$ alkyl, and
$NHCOOR^7$ wherein $R^7$ is $C_1$–$C_2$ alkyl; and $R^2$ and $R^3$ are each independently $C_1$–$C_{12}$ alkyl, $C_5$–$C_6$ cycloalkyl or benzyl; or $R^2$ and $R^3$ taken together are tetramethylene, pentamethylene, oxydiethylene or thiodiethylene.

2. A compound in accordance with claim 1 wherein $R^1$ is phenyl or phenyl substituted with one or more members selected from the group consisting of:
chlorine,
methyl,
methoxy,
methylthio,
dimethylamino,
isocyanato,
methoxycarbonyl,
methoxycarbonylamino; and $R^2$ and $R^3$ are the same and are $C_1$–$C_4$ alkyl, cyclohexyl or benzyl; or $R^2$ and $R^3$ taken together are oxydiethylene.

3. A compound in accordance with claim 2 wherein $R^1$ is phenyl substituted with $C_1$ to $C_2$ alkyl and $R^2$ and $R^3$ are methyl.

* * * * *